United States Patent

Lang et al.

[11] Patent Number: 5,972,323
[45] Date of Patent: Oct. 26, 1999

[54] HYDROLYTICALLY CLEAVABLE ACTIVE INGREDIENT DERIVATIVE COMPOUNDS, HAIR TREATMENT COMPOSITIONS CONTAINING THEM AND HAIR TREATMENT METHODS

[75] Inventors: Günther Lang, Reinheim; Rudolf Bimczok, Seeheim-Jugenheim; Thomas Czigler, Griesheim; Thomas Kripp, Fränkisch-Crumbach, all of Germany

[73] Assignee: Wella AG, Darmstadt, Germany

[21] Appl. No.: 08/899,842

[22] Filed: Jul. 24, 1997

[30] Foreign Application Priority Data

Aug. 6, 1996 [DE] Germany .................. 196 31 685

[51] Int. Cl.⁶ .................. A61K 7/09; A61K 7/11
[52] U.S. Cl. .................. 424/70.28; 424/70.1; 424/70.19; 424/47
[58] Field of Search .................. 424/70.1, 70.19, 424/70.28, 47

[56] References Cited

U.S. PATENT DOCUMENTS 2,429,171  10/1947  Ruzicka et al. .

FOREIGN PATENT DOCUMENTS 0 220 538     5/1987   European Pat. Off. .
0 688 555 A2 12/1995   European Pat. Off. .
657 055       2/1937   Germany .

OTHER PUBLICATIONS

M. Metayer et al.,: "Preparation et Proprietes Pharmacodynamiques de Quelques Esters de la Betaine", Ann. Pharm FR, Bd. 10, 1952, pp. 437–440.

*Primary Examiner*—Jyothsna Venkat
*Attorney, Agent, or Firm*—Michael J. Striker

[57] ABSTRACT

The new active ingredient derivative compounds have the formula (I)

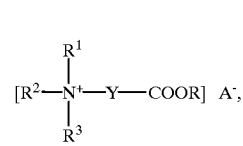

wherein $R^1$, $R^2$ and $R^3$ are the same or different and are each an unsubstituted or substituted alkyl group, Y is an unsubstituted or substituted alkylene group, R is an active ingredient group which, prior to ester formation, has at least one OH group and $A^-$ is an anion. A process for making the compounds of formula (I) is described. Hair treatment compositions containing these compounds and methods of treating hair with these hair treatment compositions are also described.

5 Claims, 1 Drawing Sheet

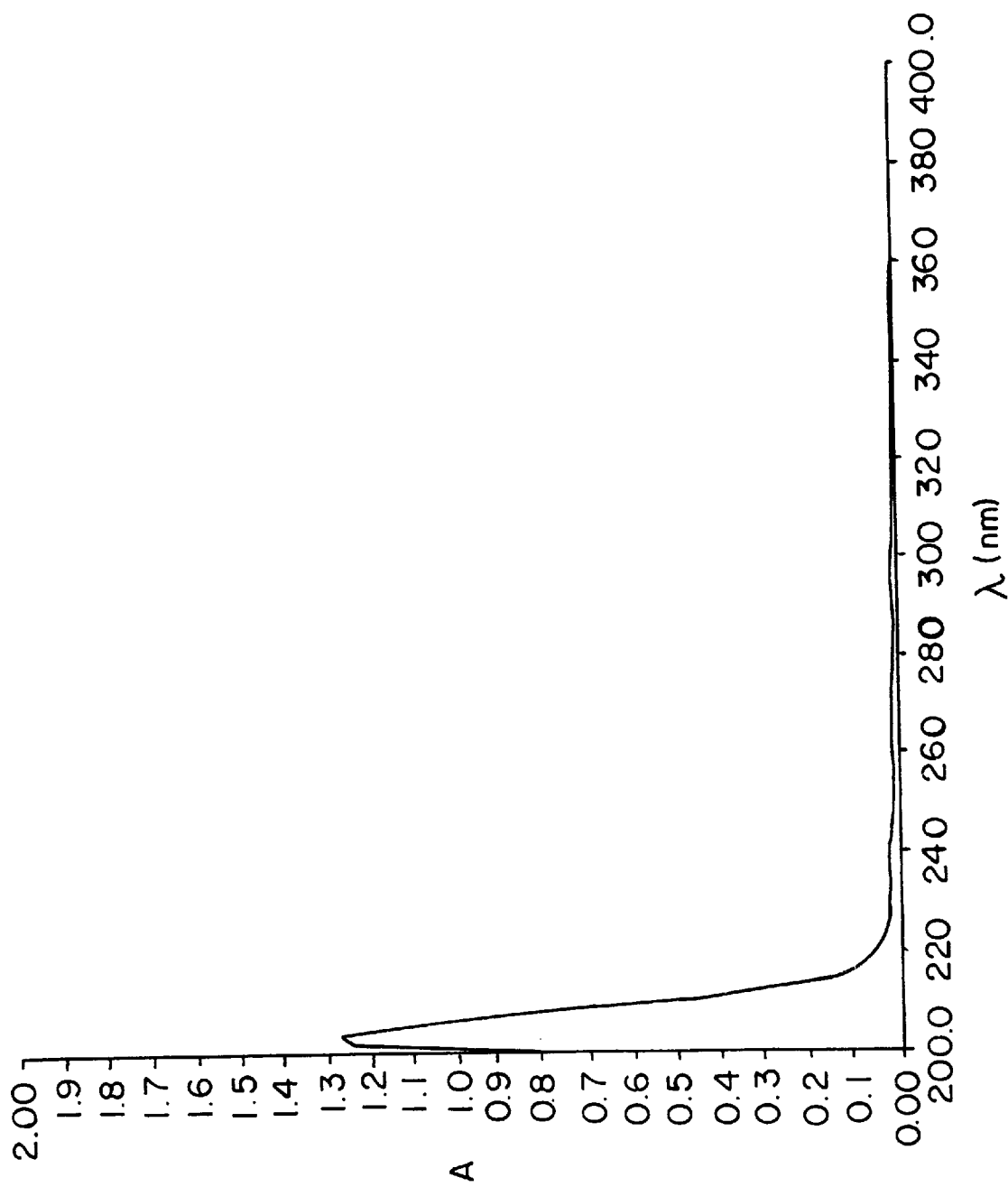

5,972,323

HYDROLYTICALLY CLEAVABLE ACTIVE INGREDIENT DERIVATIVE COMPOUNDS, HAIR TREATMENT COMPOSITIONS CONTAINING THEM AND HAIR TREATMENT METHODS

BACKGROUND OF THE INVENTION

The present invention relates to hydrolytically cleavable active ingredient derivative compounds, to hair treatment compositions containing them and to methods of treating hair with those compositions.

A number of different active ingredients are used for beautification and care of hair or for protection of hair. Some of these active ingredients only remain on the hair for a short application period (for example, permanent wave compositions) and are rinsed out of the hair afterwards, while other active ingredients remain on the hair and act on it for a certain predetermined acting time. Hair fixing compositions and hair sprays, which maintain their action until subsequent contact with water or moisture, or hair rinses and hair care compositions, which remain on the hair until subsequent washing of the hair, or temporary and/or semi-permanent hair dye compositions ("Hair tinting compositions"), which remain on the hair over a more or less extended period of time according to their service life while the intensity of color of the dyed hair decreases with each hair washing, can be named among those latter active ingredients.

To an increasing extent the need has arisen to extend the acting time of active ingredients contained in hair treatment compositions in order to provide long-term protection and/or long-term care of the hair. A special value is placed on a high resistance of the active ingredient to being washed out, so that the action of the active ingredient is maintained also after many hair washings.

Also there is an urgent requirement to make a weakly soluble or insoluble active ingredient and an active ingredient with a reduced penetration ability available for use in cosmetic compositions.

SUMMARY OF THE INVENTION

It is an object of the present invention to provide new active ingredient derivative compounds and hair treatment compositions containing them, with which the above-described requirements are most extensively fulfilled.

The new hydrolytically cleavable derivatives according to the invention have the following formula (I):

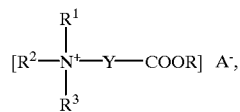
(I)

wherein $R^1$, $R^2$ and $R^3$ are the same or different and are each an unsubstituted or substituted alkyl group, Y is an unsubstituted or substituted alkylene group, R is an active ingredient group, which prior to ester formation has at least one OH group and $A^-$ is an anion.

The $R^1$, $R^2$ and $R^3$ groups are preferably $C_1$- to $C_6$-alkyl groups and especially $C_1$- to $C_4$-alkyl groups, especially methyl, ethyl, propyl, isopropyl or butyl groups. Methyl groups are particularly preferred. The above-named alkyl groups can also be substituted with one or more hydroxy or amino groups.

The Y group is preferably an unsubstituted $C_1$- to $C_6$-alkylene group, especially a —$CH_2$—, —$CH_2$—$CH_2$—, —$CH_2$—$CH_2$—$CH_2$— or —$CH_2$—$CH_2$—$CH_2$—$CH_2$— group, or a substituted $C_2$- to —$C_{10}$-alkylene group having at least one hydroxy group, amino group, acyl(especially $C_1$- to $C_2$-) group, or quaternary ammonium group, especially a substituted —$CH_2$—$CH_2$—, —$CH_2$—$CH_2$—$CH_2$— or —$CH_2$—$CH_2$—$CH_2$—$CH_2$— group.

As active ingredient group R each active ingredient group having at least one OH group prior to esterification can be used, so that, besides conventional care substances, water insoluble and/or weakly water soluble compounds can also be included, for example organophile, low molecular weight active ingredients with at least one free OH group per molecule and compounds with a reduced penetration power. The following are examples of suitable active ingredients: care ingredients (e.g. fatty alcohols, panthenol, cholesterol or farnesol), vitamins (such as vitamin A(retinol), vitamin $A_2$ (didehydroretinol), vitamin $D_2$ (calciferol), vitamin E (tocopherol), vitamin $K_1$ or $K_2$), perfumes (for example, ethyl vanillin, geraniol, nerol, linalool, α-terpineol or menthol), preservative materials and/or fungicidal or bactericidal materials (for example thymol or p-hydroxybenzoic acid ester), lipids (for example diglyceride) or dyes.

The preferred active ingredient derivative compounds of formula (I) are the active ingredient esters of L-, D- or L, D-carnitines ($R^1$, $R^2$, $R^3$=—$CH_3$ and Y=—$CH_2$—CHOH—$CH_2$—), L-,D- or L,D-O-acetyl carnitines ($R^1$,$R^2$,$R^3$=—$CH_3$ and Y=—$CH_2$—CH(OOCCH$_3$)—$CH_2$—), or betaines ($R^1$,$R^2$,$R^3$=—$CH_3$ and Y=—$CH_2$—). Preferably the anion $A^-$ is sulfate anion, phosphate anion, hydrogen phosphate anion, carbonate anion, hydrogen carbonate anion, iodide anion, chloride anion, bromide anion, oxalate anion, formate anion, acetate anion, citrate anion, tartrate anion, malate anion or pyruvate anion.

The active ingredient derivative compounds of formula (I) are easily made or synthesized by esterification of the compounds of formula (II), with an active ingredient compound as reactant that has at least one OH group per molecule:

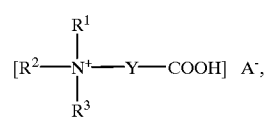
(II)

in which $R^1$, $R^2$, $R^3$, Y and $A^-$ have the same meaning as in formula (I).

The compound of formula (II) is activated by conversion into the acid chloride of formula (III) and then esterified with the active ingredient as follows:

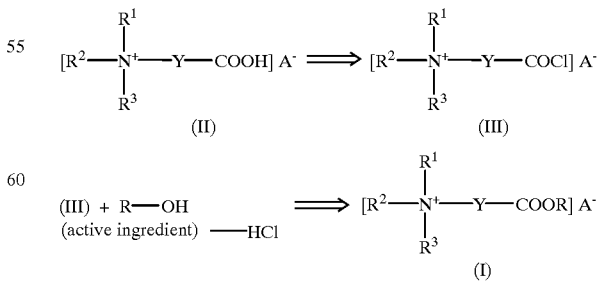

The active ingredient derivative compounds according to the invention of formula (I) enable transfer of insoluble or slightly soluble active ingredients and active ingredients with reduced penetration power into the hair and provide the hair treatment composition with a substantially improved acting time and wash out stability. Furthermore the active ingredient derivative compounds of formula I provide a clear improvement of the acting time and an increase in the wash out stability for very easily washed out active ingredients.

The subject matter of the present invention also includes a hair treatment composition which is characterized by at least one active ingredient derivative compound of formula (I).

The active ingredient derivative compounds of formula (I) are contained in the hair treatment composition according to the invention in a total amount of from 0.01 to 20 percent by weight, especially from 0.1 to 10 percent by weight.

The hair treatment composition according to the invention has a neutral to acid pH value (pH≦7), but a pH value of from 2 to 7 and especially from 5 to 6.5 is preferred.

For adjustment of the neutral to acid pH values according to the invention both organic and also inorganic acids are suitable, for example α-hydroxycarboxylic acids, such as glycolic acid, lactic acid, tartaric acid, citric acid or malic acid, ascorbic acid, gluconic acid, acetic acid, hydrochloric acid or phosphoric acid, as well as mixtures of the above-mentioned acids.

The amounts of the above-mentioned acids are advantageously in a range from 0.1 to 10 percent by weight, while an amount of from 0.5 to 3 percent by weight is particularly preferred.

The hair treatment composition according to the invention can also contain additional conventional ingredients which are standard in hair treatment compositions as needed, for example, perfumes; complex formers; waxes; preservatives; cosmetic resins, such as polyvinylpyrrolidone or polyvinyl acetate; thickeners; alginates; guar gum; hair care substances, such as cationic polymers or lanolin derivative compounds; or wetting agents and emulsifiers selected from the classes of anionic, nonionic, amphoteric or cationic surface active substances.

The above-mentioned ingredients are used in standard amounts suitable for their purposes, for example the wetting agents and emulsifiers in a concentration of from 0.1 to 30 percent by weight, and the care substances in an amount of from 0.1 to 5 percent by weight.

The hair treatment compositions according to the invention can contain other solvents besides water, such as aliphatic alcohols, especially ethanol or isopropanol, or glycol ether, especially 1,2-propandiol. The water content of the hair treatment compositions according to the invention amounts to from about 25 to 95 percent by weight, advantageously 30 to 85% by weight, while the content of the conventional solvents is from about 5 to 30 percent by weight.

The hair treatment composition according to the invention can be present in the form of an aqueous or aqueous-alcoholic solution, a cream, a gel, an emulsion, an aerosol spray or an aerosol foam. The hair treatment composition according to the invention can be packaged in to the form of a one component preparation and also in the form of a multicomponent preparation.

The packaging of the hair treatment composition according to the invention in the form of a two-component preparation is particularly preferred. In this two-component preparation the active ingredient derivative compound of formula (I) is packaged separately from the standard ingredients and the making of the ready-to-use hair treatment composition occurs directly prior to application by mixing both components.

The application of the above-described hair treatment composition according to the invention occurs by a method comprising applying an amount of the hair treatment composition sufficient for the hair treatment to the hair, allowing the hair treatment composition to act on the hair at 15 to 50° C. at about 1 to 60 minutes, advantageously 2 to 30 minutes, then treating the hair with an alkaline solution (pH>7, advantageously pH=8 to 9) and, after a short acting time for the alkaline solution (about 1 to 15 minutes, advantageously 2 to 10 minutes), the hair is thoroughly rinsed with water, washed with a shampoo, as needed, and subsequently dried.

Suitable alkaline solutions include especially from 0.5 to 10 percent, advantageously i to 6 percent, aqueous solutions of the following compounds: ammonia, guanidine, ammonium or alkali carbonates (for example sodium carbonate), ammonium or alkali hydrogen carbonate (for example sodium hydrogen carbonate).

During use of the active ingredient derivative compounds of formula (I), when the active ingredient groups have a comparatively high water solubility, the treatment of the hair with the alkaline solution, by which the active ingredient is split hydrolytically from the active ingredient derivative compound of formula (I), can also be abandoned in order to aid the fixing of the active ingredient by ionic bonding.

The hair treatment composition according to the invention provides an outstanding, uniform, intense and extremely lasting up-take of the active ingredient on the hair, whereby the caring, fixing, protecting or dyeing effect of the active ingredient lasts until after ten or more hair washings.

BRIEF DESCRIPTION OF THE DRAWING

The objects, features and advantages of the invention will now be illustrated in more detail with the aid of the following examples, with reference to the accompanying FIGURE in which:

The sole FIGURE is a UV spectrum of O-Acetylcarnitinyl Cholesterol.

EXAMPLES

The following examples should illustrate the subject matter according to the invention, without further limitation of the claims appended hereinbelow.

Example 1

Hair Treatment Composition (gel-like)

| | |
|---|---|
| 2.5 g | active ingredient derivative compound of formula (I) with $R^1, R^2, R^3$ = —$CH_3$; Y = —$CH_2$—CH(OOCCH$_3$)—$CH_2$—; $A^-$ =$Cl^-$ and R = the active ingredient according to the following Table 1 |
| 1.0 g | hydroxypropylmethyl cellulose |
| 0.5 g | lauryl pyridinium chloride |
| 0.3 g | perfume |
| 95.7 g | water |
| 100.0 g | |

The pH value of the hair treatment composition is adjusted to 6.0 with 10 percent by weight citric acid.

TABLE 1

| Example | Active ingredient from which R in Formula I is derived |
| --- | --- |
| 1a | lauryl alcohol (dodecanol) |
| 1b | myristyl alcohol (tetradecanol) |
| 1c | cetyl alcohol (hexadecanol) |
| 1d | vitamin A (retinol) |
| 1e | vitamin E (tocopherol) |
| 1f | panthenol |
| 1g | vitamin P (rutin) |

A) Examples 1a) to 1e)

The hair treatment composition is applied to the hair and allowed to act on the hair at 45° C. for 30 minutes. Then the hair is treated for 5 minutes with a 2 percent aqueous ammonia solution and subsequently rinsed with lukewarm water, washed with a shampoo, rinsed again with water and dried.

The care effect or action is retained after several washing without a noticeable intensity loss.

B) Examples 1f) and 1g)

The hair treatment composition is applied to the hair and allowed to act on the hair at 45° C. for 30 minutes. Subsequently the hair is rinsed with lukewarm water, washed with a shampoo, rinsed again with water and dried.

The care action of the hair treatment composition is reduced only slightly with multiple hair washings.

Example 2

Hair Treatment Composition (Two-component Package)

| Component 1: | |
| --- | --- |
| 2.1 g | sodium cocoamphoacetate (40% aqueous solution) |
| 94.9 g | water |
| 97.0 g | |
| Component 2: | |
| 3.0 g | active ingredient derivative of formula (I) with $R^1, R^2, R^3 = -CH_3$; Y = $-CH_2-CH(OOCCH_3)-CH_2-$; $A^- = Cl^-$ and R = cholesterol group. |

Both components are mixed with each other immediately prior to use. The hair is treated with the ready-to-use hair treatment composition according to the invention so obtained in the manner described in example 1a.

Example 3

Synthesis of Carnityl Active ingredient Derivative Compounds

Step 1: Activation of Carnitine 19.7 g (0.1 mol) carnitine hydrochloride are suspended in 500 ml water-free dichloromethane and mixed with stirring with dropwise addition of 11.9 g (0.15 mol) of thionyl chloride. The gradually forming acid chloride goes into solution. The solvent and unreacted thionyl chloride are distilled away. A mixture comprising carnityl chloride and oligo-O-carnitinyl carnitinyl chlorides is obtained, which can be used in step 2 without further preparation.

Step 2: Esterification of Carnitine to Carnitinyl Active Ingredient Derivative Compound(general formulation)

0.1 mol of the active ingredient to be derivatized is dissolved in 500 ml of water-free dichloromethane and reacted with stirring with a 1.5 fold excess of the carnitinyl chloride mixture from step 1 per free OH group of the active ingredient. After 6 hours stirring of the reaction mixture at room temperature 20 ml of water-free methanol are added to combine with the excess carnitinyl chloride mixture. The reaction mixture is then stirred for an additional 5 minutes. Subsequently the volatile components are distilled away. The residue obtained can be used directly in a hair treatment composition without further purification.

Example 4

Synthesis of O-Acetylcarnitinyl Effective Ingredient Derivative Compounds

Step 1: Preparation of O-Acyl Carnitine (general formulation)

The preparation of O-Acyl carnitines occurs according to standard acylation methods with activated acids.

19.7 g (0.1 mol) carnitine hydrochloride are suspended and/or dissolved in 100 ml water-free acetic acid at 40° C. The reaction mixture obtained is reacted slowly with 0.1 mol of a suitable acid chloride ($C_2$- to $C_4$-carboxylic acid chloride) and then stirred for 3 to 4 hours at 40° C. Subsequently the solvent and unreacted acid chloride are distilled away, the residue is taken up in 100 ml water-free hot isopropanol and filtered hot.

The O-acyl carnitine is obtained after concentration of the filtrate.

Yield(O-acetyl carnitine hydrochloride): 98% of theoretical.

Step 2: Activation of the Carnitine 23.9 g (0.1 mol) of O-acetyl carnitine hydrochloride are suspended with 500 ml water-free dichloromethane and mixed with stirring with dropwise addition of 11.9 g (0.15 mol) thionyl chloride. The gradually arising acid chloride goes into solution. The solvent and the unreacted thionyl chloride are distilled away. The residue obtained can be used in step 3) without additional purification.

Step 3: Esterification of O-Acyl Carnitine to O-Acyl Carnitinyl Active Ingredient Derivative Compounds (general formulation)

0.1 mol of the derivatized active ingredient is dissolved in 500 ml water-free dichloromethane and mixed with stirring with a 1.5-fold excess of the carnitinyl chloride mixture from step 2 per free OH group of the active ingredient. After 6 hours stirring of the reaction mixture at room temperature 20 ml of water-free methanol are added to combine with the excess carnitinyl chloride mixture. The reaction mixture is then stirred for an additional 5 minutes. Subsequently the volatile components are distilled away. The residue obtained can be used directly in a hair treatment composition without further purification.

O-Acetylcarnitinyl Cholesterol

The characterization occurs by UV spectroscopy with a spectrometer of Perkin-Elmer, Type Lambda 16. The resulting spectra of an ethanolic solution of O-acetyl carnitinyl cholesterol containing 20.8 mg of O-acetyl carnitine cholesterol per 100 ml ethanol is illustrated in the accompanying figure. The scanning speed was 240.00 nm/min, data interval 2.0000 nm, slit width, 1.0000 nm and the smoothing interval, 4.00 nm. The UV spectrum: A=1.27 to 1.28; $\lambda$=202 to 205.

All percentages given the above-identified disclosure are percentages by weight, unless otherwise indicated.

The disclosure in German Patent Application 196 31 685.5 of Aug. 6, 1996 is incorporated here by reference. This German Patent Application discloses the invention described hereinabove and claimed in the claims appended hereininbelow and provides the basis for a claim of priority for the instant invention under 35 U.S.C. 119.

While the invention has been illustrated and described as embodied in a hydrolytically cleavable active ingredient derivative compound, hair treatment composition containing it and method of treating hair with it, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of treating hair comprising
   a) providing an aqueous hair treatment composition having a pH of from 2 to 7 and containing water and at least one active ingredient derivative compound of formula (I)

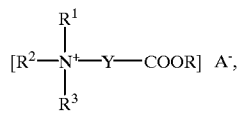

wherein $R^1$, $R^2$ and $R^3$ are the same or different and are each an unsubstituted alkyl group having from one to six carbon atoms or a substituted alkyl group having from one to six carbon atoms and one or more hydroxy or amine group substituents; Y is an unsubstituted alkylene group having from one to six carbon atoms or a substituted alkylene group having from 2 to 10 carbon atoms and at least one hydroxy group, amino group, O-acetyl group or quaternary ammonium group substituent; R is an active ingredient group of an active ingredient of the formula ROH, said active ingredient being selected from the group consisting of lauryl alcohol, myristyl alcohol, cetyl alcohol, panthenol, cholesterol, farnesol, retinol, didehydroretinol, calciferol, tocopherol, vitamin $K_1$, vitamin $K_2$, ethyl vanillin, geraniol, nerol, linalool, α-terpineol, menthol, thymol, rutin and p-hydroxybenzoic acid esters, and $A^-$ is an anion;
   b) applying an amount of said hair treatment composition sufficient to treat the hair to said hair;
   c) allowing said hair treatment composition applied to the hair in step b) to act on the hair for an acting time of from 1 to 60 minutes at 15° C. to 50° C.;
   d) after step c), treating the hair with an alkaline solution for 1 to 15 minutes; and
   e) rinsing the hair with water, and washing the hair with a shampoo as needed and drying the hair;
   wherein said alkaline solution contains from 0.5 to 10 percent by weight of a member selected from the group consisting of ammonia, guanidine, ammonium carbonate, ammonium hydrogen carbonate, alkali carbonates and alkali hydrogen carbonates.

2. The method as defined in claim 1, wherein said $R^1$, $R^2$ and $R^3$ groups are each a methyl group and said Y is selected from the group consisting of —CH$_2$—CH(OH)—CH$_2$—, —CH$_2$—CH (OOCCH$_3$)—CH$_2$— and —CH—.

3. The method as defined in claim 2, wherein said anion is selected from the group consisting of sulfate, phosphate, hydrogen phosphate, carbonate, hydrogen carbonate, iodide, chloride, bromide, oxalate, formate, acetate, citrate, tartrate, malate and pyruvate.

4. A method of treating hair with an active ingredient of formula ROH, said method comprising
   a) providing an aqueous hair treatment composition having a pH of from 2 to 7 and containing water and at least one O-acetyl carnitine ester of formula (I)

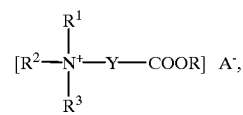

wherein $R^1$, $R^2$ and $R^3$ are each methyl groups, Y is —CH$_2$—CH(OOCCH$_3$)—CH$_2$— and R is an active ingredient group of said active ingredient of the formula ROH and said active ingredient is selected from the group consisting of lauryl alcohol, myristyl alcohol, cetyl alcohol, panthenol, cholesterol, farnesol, retinol, didehydroretinol, calciferol, tocopherol, vitamin $K_1$, vitamin $K_2$, ethyl vanillin, geraniol, nerol, linalool, α-terpineol, menthol, thymol, rutin and p-hydroxybenzoic acid esters, and $A^-$ is an anion;
   b) applying an amount of said hair treatment composition sufficient to treat the hair to said hair;
   c) allowing said hair treatment composition applied to the hair in step b) to act on the hair for an acting time of from 1 to 60 minutes at 15° C. to 50° C.;
   d) after step c), treating the hair with an alkaline solution for 1 to 15 minutes; and
   e) rinsing the hair with water, and washing the hair with a shampoo as needed and drying the hair;
   wherein said alkaline solution contains from 0.5 to 10 percent by weight of a member selected from the group consisting of ammonia, guanidine, ammonium carbonate, ammonium hydrogen carbonate, alkali carbonates and alkali hydrogen carbonates.

5. The method as defined in claim 4, wherein said anion is selected from the group consisting of sulfate, phosphate, hydrogen phosphate, carbonate, hydrogen carbonate, iodide, chloride, bromide, oxalate, formate, acetate, citrate, tartrate, malate and pyruvate.

* * * * *